United States Patent

Saito

[11] Patent Number: 5,575,780
[45] Date of Patent: Nov. 19, 1996

[54] MEDICAL HOLLOW NEEDLE AND A METHOD OF PRODUCING THEREOF

[76] Inventor: Yoshikuni Saito, Ooaza Kitanogami 1930, Kurobanemachi, Nasu-gun Tochigi-ken, Japan

[21] Appl. No.: 504,038

[22] Filed: Jul. 19, 1995

[30] Foreign Application Priority Data

Apr. 28, 1995 [JP] Japan ................................ 7-129297
Jun. 14, 1995 [JP] Japan ................................ 7-171438

[51] Int. Cl.$^6$ .................................................. A61M 5/32
[52] U.S. Cl. ............................................ 604/272; 604/264
[58] Field of Search ................................ 604/272, 264, 604/48, 57, 164, 274; 606/222, 167; 72/369

[56] References Cited

U.S. PATENT DOCUMENTS

| | | | |
|---|---|---|---|
| 1,749,919 | 3/1930 | Mierley . | |
| 2,751,907 | 6/1956 | Hickey | 128/221 |
| 3,924,617 | 12/1975 | Ferro | 128/221 |
| 4,368,738 | 1/1983 | Tersteegen et al. | 604/180 |
| 4,490,139 | 12/1984 | Huizenga et al. | 604/264 X |
| 4,565,545 | 1/1986 | Suzuki | 604/272 X |
| 5,064,411 | 11/1991 | Gordon, III | 604/48 |
| 5,484,422 | 1/1996 | Sloane, Jr. et al. | 604/272 |

*Primary Examiner*—John D. Yasko
*Attorney, Agent, or Firm*—Eckert Seamans Cherin & Mellott

[57] ABSTRACT

A medical hollow needle has a cylindrical member 2 inside which a medical liquid flow hole 25 is formed in the direction of its center axis. At a top edge portion 10 of the cylindrical member 2, a first bevel face 3 where the medical liquid flow hole 25 is open in an oblique direction, formed having a first inclined angle with respect to the axis center, is provided. At the top edge portion 10, a right bevel face 6, formed by rotating a first rotational angle in a positive direction with respect to the first bevel face 3 with the axis center as its center, having a second inclined angle with respect to the axis center is provided, and the left bevel face 7, formed by rotating a second rotational angle in an opposite direction with respect to the first bevel face 3 with the axis center as its center, having a third inclined angle with respect to the axis center, is provided. At the position opposed to the first bevel face 3 of the top edge portion 10, the sub-bevel face 12 grinded and formed in an oblique direction with respect to the axis center direction, thinning a wall thickness NA of the cylindrical member 2, is provided. A sharp edge portion 13 is comprised of at least these three bevel faces 6, 7, 12.

12 Claims, 8 Drawing Sheets

MEDICAL HOLLOW NEEDLE AND A METHOD OF PRODUCING THEREOF

BACKGROUND OF THE INVENTION

This invention relates to a medical hollow needle suitable to use as a medical hollow needle, such as a needle for hypodermic injection, dialysis, intravenous drip and blood-collecting, and a cannular needle, that is, the needle having a flow path in which a fluid, such as a liquid injection medicine and a blood, flows, and a method of producing thereof.

In a conventional method, the medical hollow needle, such as the needle for hypodermic injection, and a cannular needle has been produced by grinding a cylindrical member having a thin diameter. That is, the top end portion of the cylindrical member is grinded in an oblique direction with respect to the direction of the central axis of the cylindrical member so as to form an open bevel end face open in an oblique direction with respect to the direction of the central axis of the cylindrical member, in this way the medical hollow needle has been produced.

It is known that the thinner the wall thickness of a top edge portion of the cylindrical member is made, that is, the thinner the sharp edge portion of a medical hollow needle is made, the less blood vessel at the injection part of a patient or the like is hurt, and the less pain the patient feels at the injection part, at the time of injection or the like. In a conventional medical hollow needle, in order to extremely make a sharp edge portion thin, when an open bevel end face is grinded and formed, there is such an idea that grinding is performed in such a manner that the inclined angle of the open bevel end face to the center axis direction of the cylindrical member is extremely made small. However, in order to grind extremely making the inclined angle of the open bevel end face small, the area for forming the open bevel end face in the center axis direction of the medical hollow needle, that is, the area for grinding the cylindrical member becomes to be wider. As the result, the strength of the medical hollow needle is decreased since the cylindrical member becomes to be wide for its broad area. That is, it was difficult to extremely make the sharp edge portion thin without decreasing the strength of the medical hollow needle.

An object of the present invention is to provide a medical hollow needle and a method of producing thereof capable of extremely making a sharp edge portion thin without marring the strength of a medical hollow needle, taking the above-mentioned circumstances into consideration.

SUMMARY OF THE INVENTION

Of the present invention, the 1st invention comprises a medical hollow needle comprising:

a cylindrical member having a flow path capable of passing a fluid therein in its axis center direction;

a first bevel grinding face formed at a top end portion of said cylindrical member, such that said flow path is open in an oblique direction, having a first inclined angle with respect to said center axis;

a second bevel grinding face formed by rotating a first rotational angle in a positive direction with respect to said first bevel grinding face with said center axis as its center, having a second inclined angle with respect to said center axis, and a third bevel grinding face formed by rotating a second rotational angle in an opposite direction with respect to said first bevel grinding face with said axis center as its center, having a third inclined angle with respect to said center axis, both formed at said top edge portion of said cylindrical member;

a fourth bevel grinding face grinded and formed at a position opposed to said first bevel grinding face of said top edge portion of said cylindrical member in an oblique direction with respect to said center axis direction of said cylindrical member, thinning wall thickness of said cylindrical member; and a sharp edge portion comprised of at least three grinding faces, that is, said second, said third and said fourth bevel grinding faces.

With this invention, the fourth bevel grinding face is provided in addition to the second and the third bevel grinding faces, thereby the sharp edge portion is extremely thin. Therefore, when the medical hollow needle according to the present invention having the thin sharp edge portion, thinning the wall thickness of the top edge portion, is used, a patient or the like hardly gets hurt in blood vessel at the injection part at the time of execution of injection (that is, since the sharp edge portion is thin and sharp, injury of blood vessel or the like attendant on a stick action is kept at a minimum.), and he can hardly feel the pain at the injection part. Furthermore, since in the medical hollow needle according to the 1st invention, the sharp edge portion is comprised of at least three grinding faces, that is, the second, the third, the fourth bevel grinding faces, the sharp edge portion is located offsetting on the center axis side of the cylindrical member for the fourth bevel grinding face in comparison with a conventional medical hollow needle. Then, when the medical hollow needle according to the present invention is inserted into a blood vessel, the sharp edge portion is located extremely leaving from the inner wall of the blood vessel. As the result, the sharp edge portion is extremely prevented from sticking into the inner wall of a blood vessel, and the pain owing to the injury of the inner wall of a blood vessel and the hurt of a blood vessel is extremely saved. In particular, the pain felt at the portion where a needle is stuck into was a big difficulty in dialysis in which sticking actions by a needle are frequently performed. However, when the medical hollow needle according to the present invention is used as a needle for dialysis, the pain felt at the portion where the needle is stuck into becomes to be little, thereby the difficulty at the time of dialysis can be widely lightened.

Besides, since the sharp edge portion is extremely thin, thinning the wall thickness in the top edge portion of the cylindrical member by providing the fourth bevel grinding face even if the inclined angle of the second and the third bevel grinding faces to the center axis direction is not extremely made small, the sharp edge portion can be made thin without broadening the area for forming each bevel grinding face in the center axis direction of the medical hollow needle (for instance, the second length L2 and the like), that is the area for grinding the cylindrical member. Then, the cylindrical member is not thin for its broad area, thereby the strength of the medical hollow needle is not decreased. That is, the medical hollow needle of the present invention is one having the sharp edge portion which becomes to be extremely thin, which strength is not decreased.

When the medical hollow needle according to the 1st invention is used as a metallic needle for a remaining needle, the following effects are exercised.

That is, a remaining needle is assembled in such a manner that a metallic needle and a tube needle made of synthetic resins, such as Teflon, of its outside are independently produced in advance, and in the last routine the metallic needle is inserted into the tube needle. However, there is such a problem that in a conventional metallic needle, when the metallic needle is inserted into the tube needle, the sharp edge portion (that is, the cutting edge) of the metallic needle is stuck into the inner wall of the tube needle for the reason the inner diameter of the tube needle is extremely small, then the tube needle damages. However, in the metallic needle of the medical hollow needle according to the present invention, the sharp edge portion is comprised of at least three grinding faces, that is, the second, the third, and the fourth bevel grinding faces, thereby the sharp edge portion is located offsetting on the center axis side of the cylindrical member for the forming of the fourth bevel grinding face in comparison with a conventional metallic needle. Therefore, when the metallic needle is inserted into the tube needle, the sharp edge portion of the metallic needle is extremely prevented from being stuck into the inner wall of the tube needle since the sharp edge portion is located extremely leaving from the inner wall of the tube needle, then the damage of the tube needle is extremely saved.

Of the present invention, the 2nd invention comprises the medical hollow needle of the 1st invention, wherein said sharp edge portion is comprised of four grinding faces, that is, said first, said second, said third and said fourth bevel grinding faces.

With this invention, the effects similar to ones in the 1st invention are exercised.

Of the present invention, the 3rd invention comprises the medical hollow needle of the 1st invention, wherein said fourth bevel grinding face is a part of a tapered grinding face with said center axis as its center.

With this invention, at the portion formed the fourth bevel grinding face, near the sharp edge portion, in particular in the peripheral direction of the cylindrical member, a non-grinding face (the outer peripheral face of the cylindrical member that is not the first, the second, the third or the fourth bevel grinding face, and the like) is not left adjacent to the fourth bevel grinding face and the like. Therefore, in addition to the effects of the 1st invention, since a stepped portion or the like is not formed in such a state that the fourth bevel grinding face adjoins the non-grinding face, the pain at the time of injection can be further saved, conveniently.

Of the present invention, the 4th invention comrises the medical hollow needle of the 1st invention, wherein said fourth bevel grinding face is in the shape of a plane.

With this invention, at the portion formed the fourth bevel grinding face, near the sharp edge portion, in particular in the peripheral direction of the cylindrical member, a non-grinding face (the outer peripheral face of the cylindrical member that is not the first, the second, the third or the fourth bevel grinding face, and the like) is left adjacent to the fourth bevel grinding face and the like. That is, in addition to the effects of the 1st invention, since the non-grinding face is left near the sharp edge portion, the strength near the sharp edge portion of the medical hollow needle is extremely increased. Besides, since the non-grinding face is left near the sharp edge portion and the strength near the sharp edge portion is not decreased, the inclined angle K4 to the center axis of the fourth bevel grinding face can be extremely made small (then, the area formed the fourth bevel grinding face in the center axis direction can be made wider) so as to further make the sharp edge portion thin.

Of the present invention, the 5th invention comprises the medical hollow needle of the 1st invention, wherein said sharp edge portion is formed positioning on an inner wall forming said flow path of said cylindrical member.

With this invention, the ridgeline portion 16 or the like by the second and the third bevel grinding faces is prevented from forming at the portion of wall thickness of the cylindrical member of the sharp edge portion, then the sharp edge portion is extremely sharp formed. Therefore, in addition to the effects of the 1st invention, the sharp edge portion is extremely sharp formed, thereby the pain at the time of injection can be further saved, conveniently.

Of the present invention, the 6th invention comprises the medical hollow needle of the 1st invention, wherein said fourth bevel grinding face is formed at an inclined angle 2–15 degrees with respect to said center axis direction of said cylindrical member.

With this invention, in addition to the effects of the 1st invention, the sharp edge portion is formed in a proper state in its sharpness and strength, conveniently.

Of the present invention, the 7th invention comprises the medical hollow needle of the 1st invention, wherein said second and said third inclined angles are equal to each other.

With this invention, in addition to the effects of the 1st invention, the form of the sharp edge portion is formed equally in right and left, conveniently.

Of the present invention, the 8th invention comprises the medical hollow needle of the 1st invention, wherein said first and said second rotational angles are equal to each other.

With this invention, in addition to the effects of the 1st invention, the form of the sharp edge portion is formed equally in right and left, conveniently.

Of the present invention, the 9th invention comprises a method of producing a medical hollow needle, said method comprising:

performing a grinding machining on a top edge portion of a cylindrical member formed a flow path capable of passing a fluid therein in its center axis direction so as to form a tapered first grinding face reducing an outer diameter toward a top edge direction of said cylindrical member by thinning a wall thickness of said cylindrical member;

performing a grinding machining on said top edge portion of said cylindrical member formed said first grinding face in an oblique direction having a first inclined angle with respect to said center axis so as to form a first bevel grinding face in which said flow path is open in an oblique direction;

performing a grinding machining on said top edge portion of said cylindrical member by rotating a first rotational angle in a positive direction with respect to said first bevel grinding face with said axis center as its center, having a second inclined angle with respect to said center axis so as to form a second bevel grinding face, and by rotating a second rotational angle in an opposite direction with respect to said first bevel grinding face with said axis center as its center, having a third inclined angle with respect to said center axis so as to form a third bevel grinding face, respectively; and forming a sharp edge portion comprised of at least three grinding faces, that is, said second and said third bevel grinding faces, and said fourth bevel grinding face left without being grinded by said grinding machining of said first, said second and said third bevel grinding faces of said first grinding face.

With this invention, the fourth bevel grinding face is formed as well as the second and the third bevel grinding faces and the like, different from a conventional medical needle, and the sharp edge portion is comprised of at least these three grinding faces, thereby the sharp edge portion becomes to be extremely thin.

That is, the sharp edge portion becomes to be extremely thin by the fourth bevel grinding face left without being grinded of the first grinding face by forming the first grinding face even if grinding machining is performed so as not to make the inclined angle of the second and the third bevel grinding faces to the center axis direction small. Therefore, the sharp edge portion can be made thin without broadening the area for forming the first, the second, the third, and the fourth bevel grinding faces in the center axis direction of the medical hollow needle, that is, the area for grinding the cylindrical member. Then, the cylindrical member is not made thin for its broader area, and the strength of the medical hollow needle is not decreased. That is, in the method of producing of the present invention, the sharp edge portion can be extremely made thin without decreasing the strength of the medical hollow needle.

Besides, since the fourth bevel grinding face is a part of the tapered first grinding face with the center axis as its center, the non-grinding face (the outer peripheral face of the cylindrical member which is not the first, the second, the third or the fourth grinding face, and the like) is not left adjacent to the fourth bevel grinding face and the like at the portion formed the fourth bevel grinding face, near the sharp edge portion, in particular in the peripheral direction of the cylindrical member. Then, a stepped portion or the like is not formed in such a state that the fourth bevel grinding face adjoins the non-grinding face, thereby the pain at the time of injection can be further saved, conveniently.

When grinding is performed on the first, the second, the third bevel grinding faces and the like, the top end portion which is a grinded portion, receives a high heat if the quantity of grinding of one time is more, thereby the material of the top end portion is often softened. When the material of the top end portion is softened, such an inconvenience that the top end portion is chipped off, occurs at the time of bur removing work after grinding. However, in the method of producing according to the present invention, the top end portion is grinded so as to form the first grinding face, thereafter the grinding on the first, the second and the third bevel grinding faces is performed. Then, when the first, the second and the third bevel grinding faces are grinded, the quantity of grinding is reduced since the first grinding face is already grinded. Therefore, the top end portion is prevented from receiving a high heat and softening for the reduced quantity of grinding. Then, such an inconvenience that the top end portion is chipped off at the time of bur removing work after grinding is extremely saved.

Of the present invention, the 10th invention comprises a method of producing a medical hollow needle, said method comprising:

grinding a top edge portion of a cylindrical member formed a flow path capable of passing a fluid therein in its center axis direction, in an oblique direction with respect to said center axis direction of said cylindrical member, thinning wall thickness of said cylindrical member, so as to form a fourth bevel grinding face in the shape of a plane;

performing a grinding machining on a portion opposed to said fourth bevel grinding face of said top edge portion of said cylindrical member formed said fourth bevel grinding face, in an oblique direction, having a first inclined angle with respect to said center axis so as to form a first bevel grinding face in which said flow path is open in an oblique direction;

performing a grinding machining on said top edge portion of said cylindrical member by rotating a first rotational angle in a positive direction with respect to said first bevel grinding face with said axis center as its center, having a second inclined angle with respect to said center axis so as to form a second bevel grinding face, and by rotating a second rotational angle in an opposite direction with respect to said first bevel grinding face with said axis center as its center, having a third inclined angle with respect to said center axis so as to form a third bevel grinding face, respectively; and forming a sharp edge portion comprised of at least said second, said third and said fourth bevel grinding faces.

With this invention, the sharp edge portion becomes to be extremely thin since the fourth bevel grinding face is formed as well as the second and the third bevel grinding faces and the like, different from a conventional medical hollow needle, and the sharp edge portion is comprised of at least these three grinding faces.

That is, the sharp edge portion becomes to be extremely thin by the fourth bevel grinding face by forming the fourth bevel grinding face even if grinding machining is performed so as not to make the inclined angle of the second and the third bevel grinding faces to the center axis direction of the cylindrical member small. Therefore, the sharp edge portion can be made thin without broadening the grinding area of the medical hollow needle in the center axis direction, that is, the area for grinding the cylindrical member. Then, since the cylindrical member is not made thin for its broader area, the strength of the medical hollow needle is not decreased. That is, in the method of producing of the present invention, the sharp edge portion can be extremely made thin without decreasing the strength of the medical hollow needle.

Besides, since in the method of producing in the present invention, the first, the second, the third and the fourth bevel grinding faces are grinded in an oblique direction with respect to the axis center direction of the cylindrical member, for instance, it is not necessary to perform a cylindrical grinding or the like. Therefore, in the method of producing of the present invention, a grinding machining can be performed with only a grinding machine, such as the grinding machine for forming bevel face grinding (known) which is used when a conventional medical hollow needle is produced, in which grinding is performed by rotating a grinding stone in the shape of a disc, without using the other machines, such as a cylindrical grinder, conveniently.

Furthermore, since the fourth bevel grinding face is formed in the shape of a plane, the non-grinding face (the outer peripheral face of the cylindrical member which is not the first, the second, the third or the fourth bevel grinding face, and the like) is left adjacent to the fourth bevel grinding face in the portion formed the fourth bevel grinding face, near the sharp edge portion, in particular in the peripheral direction of the cylindrical member. Therefore, the strength near the sharp edge portion of the medical hollow needle is extremely increased. Besides, since the non-grinding face is left near the sharp edge portion and the strength near the sharp edge portion is not decreased, the inclined angle K4 of the fourth bevel grinding face to the center axis can be extremely made small (that is, the area formed the fourth bevel grinding face in the center axis direction can be made wider) so as to further make the sharp edge portion thin.

Of the present invention, the 11th invention comprises a method of producing a medical hollow needle, said method comprising:

performing a grinding machining on a top edge portion of a cylindrical member formed a flow path capable of passing a fluid therein in its center axis direction, in an oblique direction having a first inclined angle with respect to said center axis so as to form a first bevel grinding face in which said flow path is open in an oblique direction;

performing a grinding machining on said top edge portion of said cylindrical member by rotating a first rotational angle in a positive direction with respect to said first bevel grinding face with said axis center as its center, having a second inclined angle with respect to said center axis so as to form a second bevel grinding face, and by rotating a second rotational angle in an opposite direction with respect to said first bevel grinding face with said axis center as its center, having a third inclined angle with respect to said center axis so as to form a third bevel grinding face, respectively; and grinding a position opposed to said first bevel grinding face of said top edge portion of said cylindrical member in an oblique direction with respect to said center axis, thinning wall thickness of said cylindrical member so as to form a fourth bevel grinding face in the shape of a plane; and forming a sharp edge portion comprised of at least said second, said third and said fourth bevel grinding faces.

With this invention, in addition to the effects of the 10th invention, the work steps till the first, the second and the third bevel grinding faces are formed are almost similar to the producing steps of a conventional medical hollow needle, thereby a production line of a conventional medical hollow needle is easily applicable, conveniently.

Of the present invention, the 12th invention comprises a method of producing a medical hollow needle, said method comprising:

performing a grinding machining on a top edge portion of a cylindrical member formed a flow path capable of passing a fluid therein in its center axis direction, in an oblique direction having a first inclined angle with respect to said center axis so as to form a first bevel grinding face in which said flow path is open in an oblique direction;

grinding a position opposed to said first bevel grinding face of said top edge portion of said cylindrical member in an oblique direction with respect to said center axis direction, thinning wall thickness of said cylindrical member so as to form a fourth bevel grinding face in the shape of a plane;

performing a grinding machining on said top edge portion of said cylindrical member by rotating a first rotational angle in a positive direction with respect to said first bevel grinding face with said axis center as its center, having a second inclined angle with respect to said center axis so as to form a second bevel grinding face, and by rotating a second rotational angle in an opposite direction with respect to said first bevel grinding face with said axis center as its center, having a third inclined angle with respect to said center axis so as to form a third bevel grinding face, respectively; and forming a sharp edge portion comprised of at least said second, said third and said fourth bevel grinding faces.

With this invention, in addition to the effects of the 10th invention, the work steps till the first bevel grinding face is formed are almost similar to the producing steps of a conventional medical hollow needle, thereby a production line of a conventional medical hollow needle is easily applicable, conveniently.

Of the present invention, the 13th invention comprises a method of producing a medical hollow needle, said method comprising:

performing a grinding machining on a top edge portion of a cylindrical member formed a flow path capable of passing a fluid therein in its center axis direction by rotating a first rotational angle in a positive direction with respect to a predetermined standard position with said axis center as its center, having a second inclined angle with respect to said center axis so as to form a second bevel grinding face, and by rotating a second rotational angle in an opposite direction with respect to said standard position with said axis center as its center, having a third inclined angle with respect to said center axis so as to form a third bevel grinding face, respectively;

grinding a position opposed to said standard position of said top edge portion of said cylindrical member in an oblique direction with respect to said center axis direction, thinning wall thickness of said cylindrical member so as to form a fourth bevel grinding face in the shape of a plane;

performing a grinding machining on said top edge portion of said cylindrical member at said standard position in an oblique direction, having a first inclined angle with respect to said center axis so as to form a first bevel grinding face in which said flow path is open in an oblique direction; and forming a sharp edge portion comprised of at least said second, said third, and said fourth bevel grinding faces.

With this invention, in addition to the effects of the 10th invention, the work steps till the second and the third bevel grinding faces are formed are almost similar to the producing steps of a conventional medical hollow needle, thereby a production line of a conventional medical hollow needle is easily applicable, conveniently.

Of the present invention, the 14th invention comprises a method of producing a medical hollow needle, said method comprising:

performing a grinding machining on a top edge portion of a cylindrical member formed a flow path capable of passing a fluid therein in its center axis direction by rotating a first rotational angle in a positive direction with respect to a predetermined standard position with said axis center as its center, having a second inclined angle with respect to said center axis so as to form a second bevel grinding face, and by rotating a second rotational angle in an opposite direction with respect to said standard position with said axis center as its center, having a third inclined angle with respect to said center axis so as to form a third bevel grinding face, respectively;

performing a grinding machining on said top edge portion of said cylindrical member at said standard position in an oblique direction, having a first inclined angle with respect to said center axis so as to form a first bevel grinding face in which said flow path is open in an oblique direction;

grinding a position opposed to said first bevel grinding face of said top edge portion of said cylindrical member in an oblique direction with respect to said center axis direction, thinning wall thickness of said cylindrical member so as to form a fourth bevel grinding face in the shape of a plane; and forming a sharp edge portion comprised of at least said second, said third, and said fourth bevel grinding faces.

With this invention, in addition to the effects of the 10th invention, the work steps till the first, the second and the third bevel grinding faces are formed are almost similar to the producing steps of a conventional medical hollow needle, thereby a production line of a conventional medical hollow needle is easily applicable, conveniently.

Of the present invention, the 15th invention comprises the method of producing the medical hollow needle of the 9th, the 10th, the 11th, the 12th, the 13th or the 14th invention wherein said sharp edge portion is formed positioning on an inner wall forming said flow path of said cylindrical member.

With this invention, the ridgeline portion 16 or the like by the second and the third bevel grinding faces is prevented from forming at the portion of wall thickness of the cylindrical member of the sharp edge portion, then the sharp edge portion is extremely sharply formed. Therefore, in addition to the effects of the 9th, the 10th, the 11th, the 12th, the 13th or the 14th invention, the sharp edge portion is extremely sharply formed, thereby the pain at the time of injection can be further saved, conveniently.

Of the present invention, the 16th invention comprises the method of producing the medical hollow needle of the 9th, the 10th, the 11th, the 12th, the 13th or the 14th invention wherein said fourth bevel grinding face is grinded with an inclined angle of 2–15 degrees with respect to said center axis direction of said cylindrical member.

With this invention, in addition to the effects of the 9th, the 10th, the 11th, the 12th, the 13th or the 14th invention, the sharp edge portion is formed in a proper state in its sharpness and strength, conveniently.

Of the present invention, the 17th invention comprises the method of producing the medical hollow needle of the 9th, the 10th, the 11th, the 12th, the 13th or the 14th invention wherein said second and third inclined angles are equal to each other.

With this invention, in addition to the effects of the 9th, the 10th, the 11th, the 12th, the 13th or the 14th invention, the form of the sharp edge portion is formed equally in right and left, conveniently.

Of the present invention, the 18th invention comprises the method of producing the medical hollow needle of the 9th, the 10th, the 11th, the 12th, the 13th or the 14th invention wherein said first and said second rotational angles are equal to each other.

With this invention, in addition to the effects of the 9th, the 10th, the 11th, the 12th, the 13th or the 14th invention, the form of the sharp edge portion is formed equally in right and left, conveniently.

Of the present invention, the 19th invention comprises the medical hollow needle of the 1st invention, wherein a fifth bevel grinding face is provided at an apical portion of an outer peripheral face side of said cylindrical member of a first intersectional portion formed by crossing said first bevel grinding face and said second bevel grinding face, by removing said apical portion, and a sixth bevel grinding face is provided at an apical portion of an outer peripheral face side of said cylindrical member of a second intersectional portion formed by crossing said first bevel grinding face and said third bevel grinding face, by removing said apical portion.

With this invention, in addition to the effects of the 1st invention, since the fifth and the sixth bevel grinding faces are provided by respectively removing the both sides of apical portions in the medical hollow needle according to the 19th invention before-mentioned, the insertion resistance with the medical hollow needle is lower than one in which both sides of apical portions are not removed. That is, when the medical hollow needle according to the 19th invention is stuck into a human body or the like at the time of execution of injection, the resistance to a skin or a blood vessel tissu is small for not providing both sides of the apical portions, thereby the hurt of the skin and the blood vessel tissu is hardly caused, then a patient hardly feels pain at the injection part.

DESCRIPTION OF THE PREFERRED EMBODIMENT

Embodiments of the present invention will now be described hereinafter with respect to the accompanying drawings.

Figure 1:
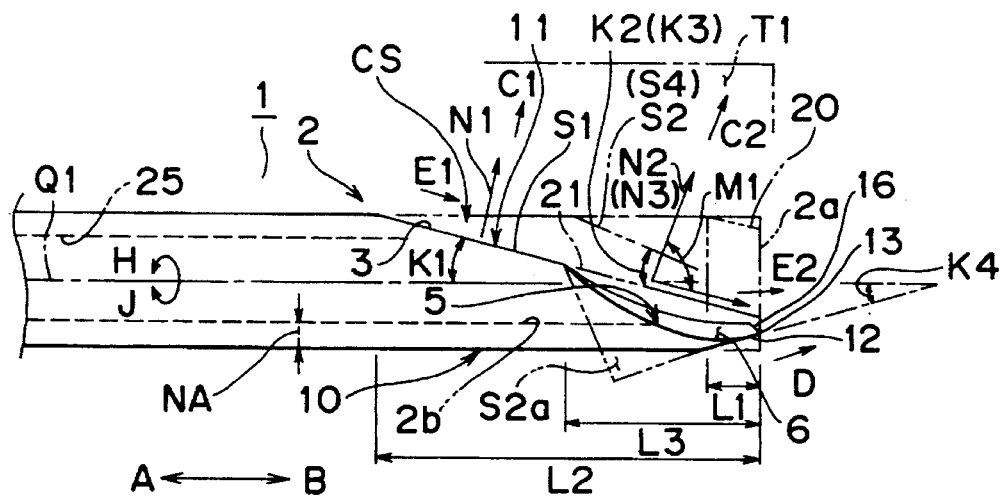
FIG. 1 is a side view showing an example of a medical hollow needle according to the present invention.
Figure 2:
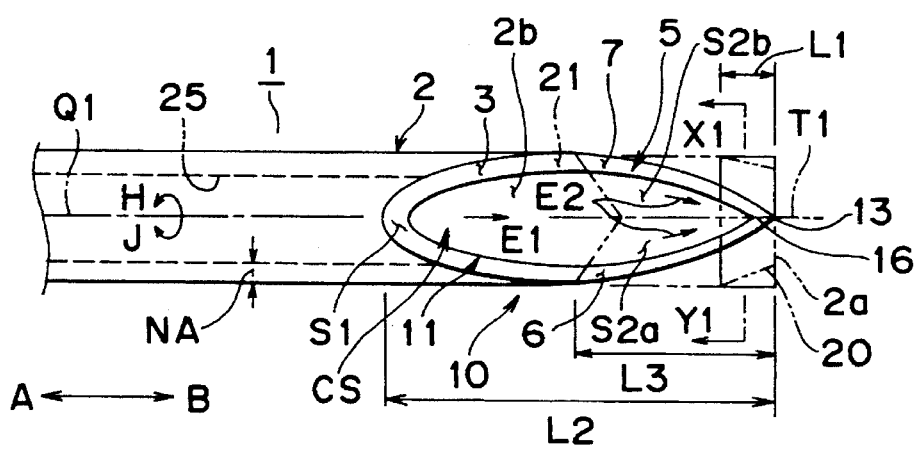
FIG. 2 is a view seen from upper hand of FIG. 1.
Figure 4:
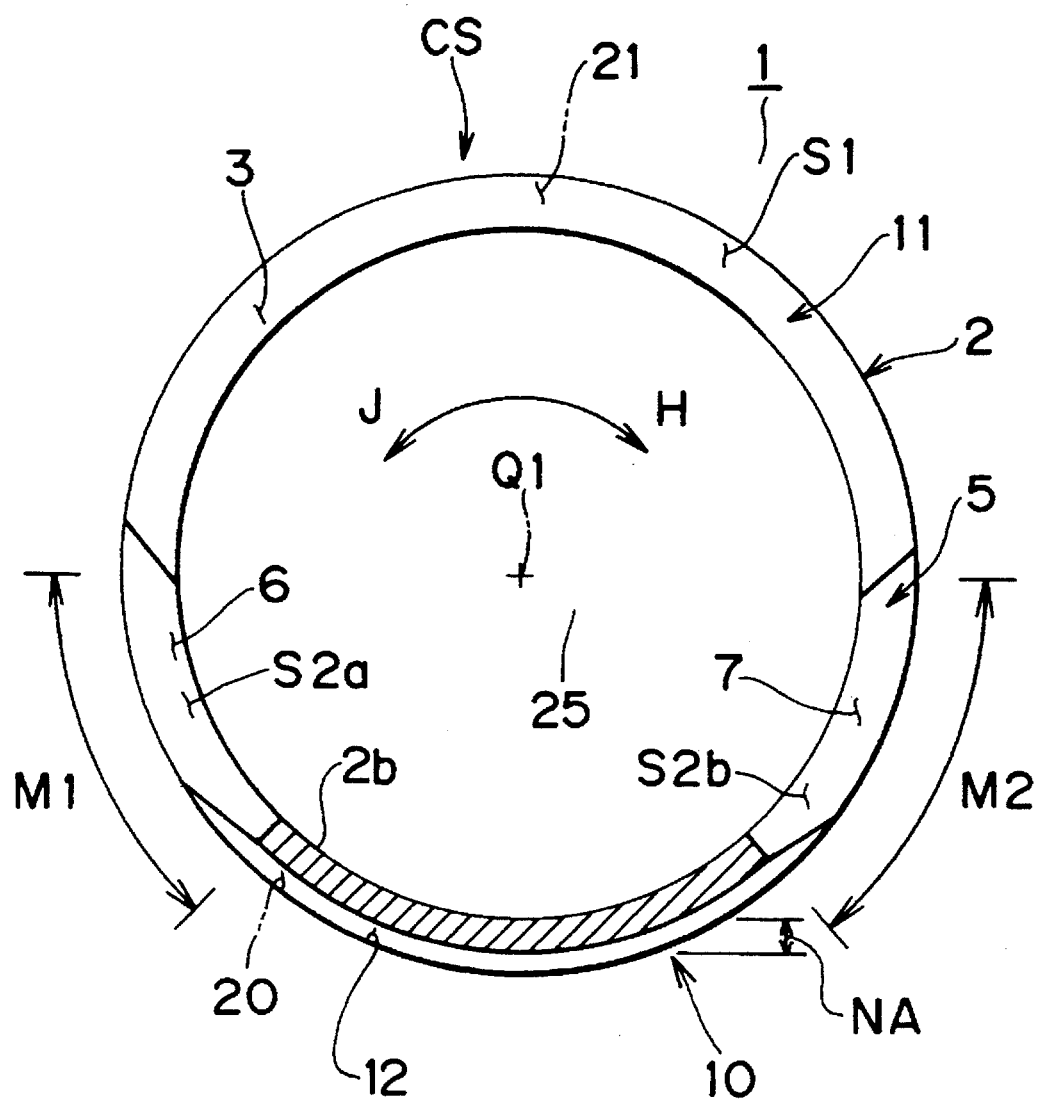
FIG. 4 is a sectional view of line X1–Y1 of FIG. 2.

A medical needle 1, or an example of a medical hollow needle according to the present invention, is produced, as shown in FIG. 1, 2 or 4, by grinding a cylindrical member 2 (shown by a two-dot chain line in a part) which is a cylindrical bar-shaped member, which diameter is extremely small, extending in the directions as shown by the arrows A and B in respective figures. Inside the cylindrical member 2, a medical liquid flow hole 25 in which a fluid, such as a medical liquid for injection, can pass, is formed in the direction of an axis center Q1 of the cylindrical member 2 (or in the directions as shown by the arrows A and B).

A top end portion 10 of the cylindrical member 2 is provided with a sub-bevel face 12, positioning on the lower side of the paper of FIG. 1 and FIG. 4. The sub-bevel face 12 comprises a part of a first grinding face 20 formed by taperingly grinding a first length L1 (that is, the area in the directions as shown by the arrows A and B) of a top edge 2a side of the cylindrical member 2 (that is, the edge portion side of the arrow B side of the figure), reducing the outside diameter of the cylindrical member 2 for the direction as shown by the arrow B, coaxially with the cylindrical member 2 (that is, making the shape of a circular truncated cone brought down), then thinning a wall thickness NA of the cylindrical member 2 for the direction as shown by the arrow B. That is, the sub-bevel face 12 is positioned along the direction as shown by the arrow D in the figure which is an oblique direction with respect to the direction as shown by the arrow B, or the direction of the axis center Q1 of the cylindrical member 2 (that is, in the direction of a generatrix of a circular truncated cone by the first grinding face 20).

At the top edge portion 10 of the cylindrical member 2, a first bevel face 3 is formed, the first bevel face 3 is the portion positioned on the left side of the paper of FIG. 1 of a second grinding face 21 made by cutting the top end portion 10 of the cylindrical member 2 in such a state that the first grinding face 20 is produced, by a grinding plane S1 where the axis center Q1 of the cylindrical member 2 and a first inclined angle K1 (acute angle) intersect each other, inclining to upper left hand in FIG. 1 (In fact, the grinding plane S1 is a curved face close to a plane, but this plane S1 is explained as a plane in the present embodiment as a matter of convenience.), taking the arrow B side off. The second grinding face 21 is formed in a second length L2 of the top edge 2a side of the cylindrical member 2 (that is, the area in the directions as shown by the arrows A and B), the second length L2 is broader than the first length L1, and a center position CS showing the position of the first bevel face 3 as a matter of convenience (that is, the position on the upper hand of the axis center Q1 in the paper of FIG. 1 and FIG. 4) opposes to the sub-bevel face 12. The first bevel face 3 is formed, thereby the medical liquid flow hole 25 is open in an oblique direction in the first bevel face 3.

At the top edge portion 10 of the cylindrical member 2, the first grinding face 20 is formed. Furthermore, a second bevel face 5 formed by cutting the top edge 2a side of the cylindrical member 2 in such a state that the second grinding face 21 is formed by grinding planes S2a and S2b of the figure (these are in fact curved faces akin to a plane, similar to the grinding plane S1, but in the present embodiment each of these is explained as a plane as a matter of convenience.) is formed in a third length L3 of the top edge 2a side of the cylindrical member 2 (that is, the area in the directions as shown by the arrows A and B). The third length L3 is broader than the first length L1, and is narrower than the second length L2.

The grinding plane S2a is a plane rotating a plane S2, where the axis center Q1 of the cylindrical member 2 and a second inclined angle K2 (is an acute angle and is bigger than the first inclined angle K1) intersect each other, capable of having a normal vector N2 existing on the plane T1 (the plane along the paper in FIG. 1) the same as a normal vector N1 of the grinding plane S1 (Besides, the plane S2 is a plane inclining to the upper left in FIG. 1), a predetermined first rotational angle M1 in the direction as shown by the arrow J of FIG. 1 and FIG. 4 with the axis center Q1 as its center. And, the grinding plane S2b is a plane rotating a plane S4, where the axis center Q1 and a third inclined angle K3 (is an acute angle and is bigger than the first inclined angle K1) intersect each other, capable of having a normal vector N3 existing on the plane T1 the same as the normal vector N1 (Besides, the plane S4 is a plane inclining to the upper left in FIG. 1), a predetermined second rotational angle M2 in the direction as shown by the arrow H of FIG. 4, opposite to the direction as shown by the arrow J with the axis center Q1 as its center. In the embodiment, the second inclined angle K2 is equal to the third inclined angle K3 (then, the plane S2 and the plane S4 are the same plane, and the first rotational angle M1 and the second rotational angle M2 are equal to each other (but, the medical hollow needle according to the present invention is not limiting to only the present embodiment, for example, the second inclined angle K2 and the third inclined angle K3 may be different from each other, or the first rotational angle M1 and the second rotational angle M2 may be different from each other.).

The face made by cutting the top edge 2a side of the cylindrical member 2 in such a state that the first grinding face 20 is made, and besides, the second grinding face 21 is made, by the grinding plane S2a is a right bevel face 6, and the face made by cutting by the grinding plane S2b is a left bevel face 7. That is, the second bevel face 5 is comprised of the right bevel face 6 and the left bevel face 7. In other words, at the top edge portion 10 of the cylindrical member 2, the right bevel face 6 is formed, by rotating it the first rotational angle M1 in a positive direction (that is, the direction as shown by the arrow J) to the first bevel face 3 (that is, to the center position CS) with the axis center Q1 as its center, having the second inclined angle K2 to the axis center, and the left bevel face 7 is formed, by rotating it the second rotational angle M2 in the opposite direction (that is, the direction as shown by the arrow H) to the first bevel face 3 (that is, to the center position CS) with the axis center Q1 as its center, having the third inclined angle K3 to the axis center.

As described heretofore, at the top edge portion 10 of the cylindrical member 2, the first bevel face 3 and the second bevel face 5 are successively formed in the second length L2 in the direction as shown by the arrow B, and an open bevel end face 11 is comprised by the first bevel face 3 and the second bevel face 5. The open bevel end face 11 is also the edge portion of the medical liquid flow hole 25 inside the cylindrical member 2, therefore, the medical liquid flow hole 25 is open outside. This open direction is the direction as shown by the arrow C1 of the figure, which is the direction of the normal vector N1 of the grinding plane S1 forming the first bevel face 3, and the direction as shown by the arrow C2 in the figure, which is the direction of the vector averaging the normal vectors of the grinding planes S2a, S2b forming the second bevel face 5 (that is, the normal vector N2 of the plane S2). Then, the open bevel end face 11 is open in an oblique direction to the direction as shown by the arrow B, which is the extending direction of the top edge of the cylindrical member 2. The open bevel end face 11 is provided on the upper side of the paper of FIG. 1, as shown in FIG. 1, then the sub-bevel face 12 (the lower side. of the paper of FIG. 1) is provided on the position opposed to the open bevel end face 11.

Furthermore, the open bevel end face 11 and the sub-bevel face 12 are adjacent to each other on the top edge 2a side of the cylindrical member 2, then, a sharp edge portion 13, which is sharp in the direction as shown by the arrow B, is formed between the open bevel end face 11 and the sub-bevel face 12. That is, the sharp edge portion 13 is formed by the three grinding face, the right bevel face 6, the left bevel face 7 and the sub-bevel face 12. Then, in the medical needle 1, the sub-bevel face 12 (in a conventional medical hollow needle, the open bevel end face only) is provided as well as the open bevel end face 11, thereby the sharp edge portion 13 is extremely thin.

The medical needle 1 according to the present invention is comprised as described heretofore. The medical needle 1 is produced as follows.

At first, a grinding machining is performed on the first length L1 of the top edge portion 10 of the cylindrical member 2 with an appropriate cylindrical grinder (known) as shown in FIG. 1, coaxially to the cylindrical member 2, reducing the outside diameter of the cylindrical member 2 in the direction as shown by the arrow B, that is, thinning the wall thickness NA of the cylindrical member 2 in the direction as shown by the arrow B, so as to form the tapered first grinding face 20 (shown by a full line in part, and by a two-dot chain line in the other part).

Next, a grinding machining is performed on the top edge portion 10 of the cylindrical member 2, in such a state that the first grinding face 20 is formed, with a proper grinding machine, such as the grinding machine capable of grinding by rotating a grinding stone in the shape of a disc (known)

in an oblique direction to the direction as shown by the arrow B in figure (that is, the direction having the first inclined angle K1 to the axis center Q1), that is, in the direction as shown by the arrow E1 of the figure which is the direction along the grinding plane S1 so as to form the second, grinding face 21 in the second length L2 (then, the first bevel face 3, which is a part of the second grinding face 21, is made.).

Furthermore, the top edge portion 10 of the cylindrical member 2, in such a state that the first grinding face 20 and the second grinding face 21 are made, is grinded with the grinding machine in an oblique direction to the direction as shown by the arrow B in figure, that is, in the direction as shown by the arrow E2 in figure, which is the direction along the grinding plane S2a or the grinding plane S2b so as to form the right bevel face 6 and the left bevel face 7 in the third length L3, that is, so as to form the second bevel face 5.

The second bevel face 5 is formed by grinding, thereby a part of the second grinding face 21 (the right side of the paper of FIG. 1, that is, the portion of the third length L3) is grinded and removed, and the the first bevel face 3 which is a part of the second grinding face 21 (the left side of the paper of FIG. 1) is formed, remaining without being grinded. That is, the open bevel end face 11 comprised of the first bevel face 3 and the second bevel face 5 is formed.

This open bevel end face 11 (that is, the second grinding face 21 and the second bevel face 5) is grinded and formed, thereby a part of the first grinding face 20 (the portion on the upper side of the paper of FIG. 1) is grinded and removed, and the sub-bevel face 12 which is a part of the first grinding face 20 (the lower side of the paper of FIG. 1) is formed, remaining without being grinded. And, the sharp edge portion 13 is formed between the open bevel end face 11 and the sub-bevel face 12, then the production of the medical needle 1 finishes.

As described heretofore, in the present embodiment the medical needle 1 can be produced so as to extremely make the sharp edge portion 13 thin, thinning the wall thickness NA of the cylindrical member 2, by the sub-bevel face 12 remaining of the first grinding face 20 without being grinded since the first grinding face 20 is formed, unless grinding machining is performed so as to make the inclined angles K1, K2, K3 of the open bevel end face 11 to the direction as shown by the arrow B small. That is, the medical needle 1 having thin top edge portion can be produced without broadening the second length L2 forming the open bevel end face 11, that is, the area where the cylindrical member 2 is grinded, in the entire length in the direction of the axis center Q1 of the medical needle 1. Therefore, the cylindrical member 2 can be prevented from becoming to be thin in its broad area, then the strength of the medical needle 1 can not be impaired.

The medical hollow needle according to the present invention may be an another needle different from the medical needle 1 described heretofore. For instance, the medical hollow needle according to the present invention may be a medical needle 1P as shown in FIG. 3.

The portion different from the medical needle 1 described before of the medical needle 1P is the sub-bevel face 12, and this sub-bevel face 12 of the medical needle 1P is in the shape of a plane.

The medical needle 1P is produced as follows.

Figure 3:
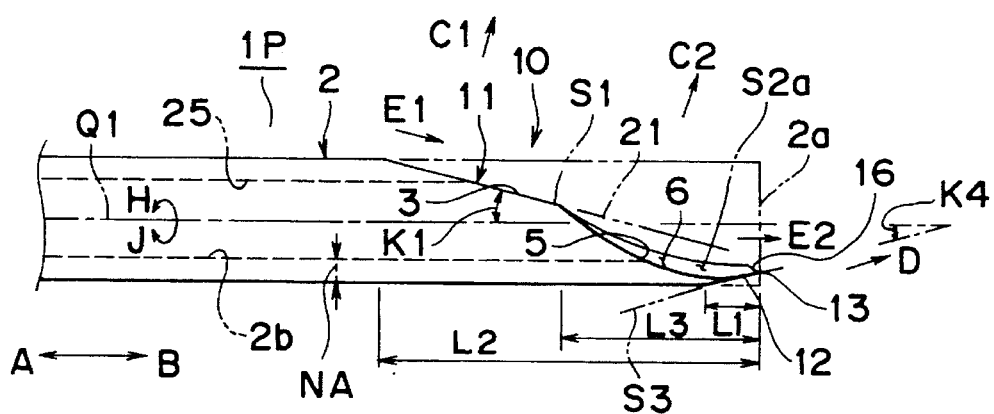
FIG. 3 is a side view showing an another example of the medical hollow needle according to the present invention.

At first, a grinding machining is performed with a proper grinding machine, such as the grinding machine capable of grinding by rotating a grinding stone in the shape of a disc (known) on the top edge portion 10 of the cylindrical member 2, as shown in FIG. 3, in an oblique direction to the direction as shown by the arrow B in the figure which is the direction of the axis center Q1 of the cylindrical member 2, that is, in the direction as shown by the arrow D of FIG. 3, thinning the wall thickness NA of the cylindrical member 2 in the direction as shown by the arrow B so as to form the sub-bevel face 12 in the shape of a plane made by cutting the top edge portion 10 of the cylindrical member 2 by a grinding plane S3 along the direction as shown by the arrow D (In fact, the sub-bevel face 12 is a curved face close to a plane as a matter of convenience of grinding, but the face 12 can be substantially dealt with a plane.).

Thereafter, in a similar way to the case of the medical needle 1 described before, with the grinding machine abovementioned, grinding machining is performed on the top edge portion 10 of the cylindrical member 2 formed the sub-bevel face 12 in an oblique direction having the first inclined angle K1 with respect to the axis center Q1 in the position opposed to the sub-bevel face 12 (that is, the center position CS of FIG. 3), that is, grinding machining is performed in the direction as shown by the arrow E1 of FIG. 3, which is the direction along the grinding plane S1 so as to form the second grinding face 21 in the second length L2 (then, the first bevel face 3, where the medical liquid flow hole 25 is open in an oblique direction, is formed as a part of the second grinding face 21.). Furthermore, the top edge portion 10 is grinded in an oblique direction with respect to the direction as shown by the arrow B in the figure, that is, in the direction as shown by the arrow E2 of the figure, which is the direction along the gringing plane S2a or S2b so as to form the right bevel face 6 and the left bevel face 7 in the third length L3, that is, so as to form the second bevel face 5, then the open bevel end face 11 is formed.

This open bevel end face 11 is grinded and formed, thereby the sharp edge portion 13 is formed between the open bevel end face 11 and the sub-bevel face 12, then the production of the medical needle 1P finishes.

The medical needle 1P may be produced by the other steps excluding ones above-mentioned.

For instance, the top edge portion 10 of the cylindrical member 2 is grinded with the grinding machine beforementioned in an oblique direction having the first inclined angle K1 with respect to the axis center Q1 in the center position CS so as to form the second grinding face 21 in the second length L2 (that is, the first bevel face 3 is formed as a part of the second grinding face 21.). Subsequently, the top edge portion 10 of the cylindrical member 2 is grinded in an oblique direction with respect to the axis center Q1, that is, in the direction as shown by the arrow E2 of the figure, which is the direction along the grinding plane S2a or the grinding plane S2b so as to form the right bevel face 6 and the left bevel face 7 in the third length L3, that is, so as to form the second bevel face 5, then the open bevel end face 11 is formed. Thereafter, the top edge portion 10 is grinded in the position opposed to the first bevel face 3 in an oblique direction with respect to the axis center Q1 in the first length L1 so as to form the sub-bevel face 12 in the shape of a plane made by cutting the top edge portion 10 of the cylindrical member 2 by the grinding plane S3 along the direction as shown by the arrow D. In this way, the sharp edge portion 13 is formed between the open bevel end face 11 and the sub-bevel face 12, then the production of the medical needle 1P finishes.

The medical needle 1P can be also produced by another steps.

For instance, the top edge portion 10 of the cylindrical member 2 is grinded with the grinding machine before-mentioned in an oblique direction having the first inclined angle K1 with respect to the axis center Q1 in the center position CS so as to form the second grinding face 21 in the second length L2 (then, the first bevel face 3 is formed as a part of the second grinding face 21.). Subsequently, the top edge portion 10 is grinded in the first length L1 in an oblique direction with respect to the axis center Q1 in the position opposed to the first bevel face 3 (then, the position opposed to the center position CS) so as to form the sub-bevel face 12 in the shape of a plane made by cutting the top edge portion 10 of the cylindrical member 2 by the grinding plane S3 along the direction as shown by the arrow D. Thereafter, the top edge portion 10 of the cylindrical member 2 is grinded in an oblique direction with respect to the axis center Q1, that is, in the direction as shown by the arrow E2 of the figure, which is the direction along the grinding plane S2a or the grinding plane S2b so as to form the right bevel face 6 and the left bevel face 7 in the third length L3, that is, so as to form the second bevel face 5, then the open bevel end face 11 is formed. In this way, the sharp edge portion 13 is formed between the open bevel end face 11 and the sub-bevel face 12, then the production of the medical needle 1P finishes.

Another steps for producing the medical needle 1P will now be explained. For instance, the top edge portion 10 of the cylindrical member 2 is grinded in the direction along the grinding plane S2a or the grinding plane S2b so as to form the right bevel face 6 and the left bevel face 7 in the third length L3, that is, so as to form the second bevel face 5. Subsequently, the top edge portion 10 is grinded in the position opposed to the second bevel face 5 (then, the position opposed to the center position CS) in the first length L1 so as to form the sub-bevel face 12 in the shape of a plane made by cutting the top edge portion 10 of the cylindrical member 2 by the grinding plane S3. Thereafter, the top edge portion 10 is grinded in an oblique direction having the first inclined angle K1 with respect to the axis center Q1 in the position opposed to the sub-bevel face 12 (then, the center position CS) so as to form the first bevel face 3. In this way, the sharp edge portion 13 is formed between the open bevel end face 11 and the sub-bevel face 12, then, the production of the medical needle 1P finishes.

Further another steps for producing the medical needle 1P are as follows. For instance, the top edge portion 10 of the cylindrical member 2 is grinded in the direction along the grinding plane S2a or the grinding plane S2b so as to form the right bevel face 6 and the left bevel face 7 in the third length L3, that is, so as to form the second bevel face 5. Subsequently, the top edge portion 10 is grinded in an oblique direction having the first inclined angle K1 with respect to the axis center Q1 in the center position CS so as to form the first bevel face 3. Thereafter, the top edge portion 10 is grinded in the first length L1 in the position opposed to the first bevel face 3 (then, the position opposed to the center position CS) so as to form the sub-bevel face 12 in the shape of a plane made by cutting the top edge portion 10 of the cylindrical member 2 by the gringing plane S3. In this way, the sharp edge portion 13 is formed between the open bevel end face 11 and the sub-bevel face 12, then the production of the medical needle 1P finishes.

The medical hollow needle according to the present invention may have an another form except the medical needles 1, 1P as shown in respective embodiments above-mentioned.

Figure 5:
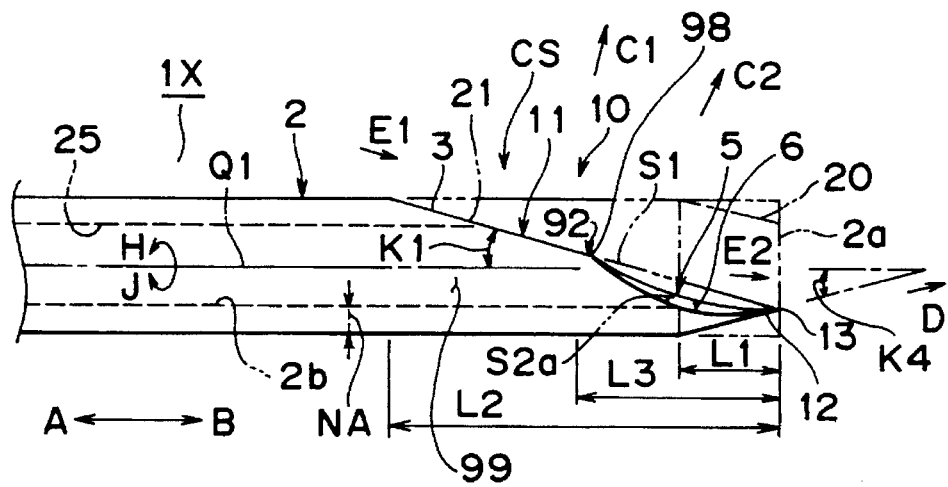
FIG. 5 is a side view showing an another example of the medical hollow needle according to the present invention.
Figure 6:
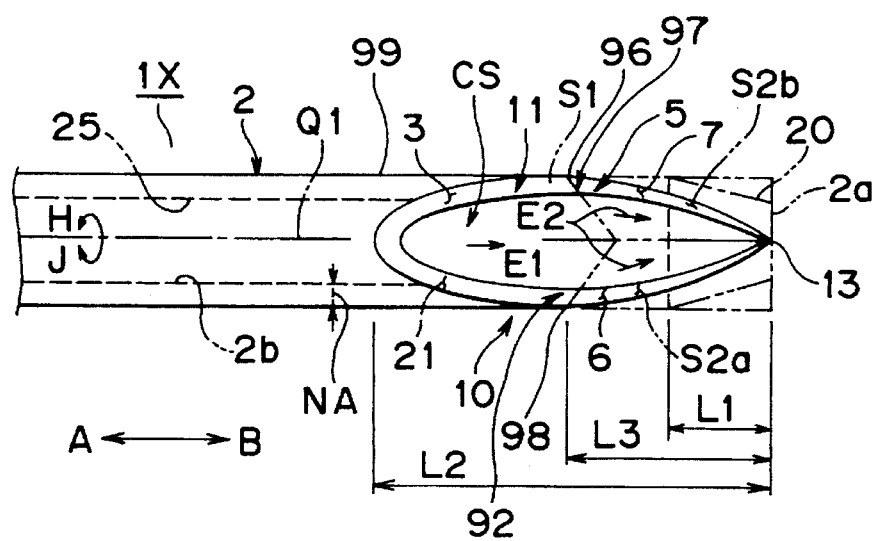
FIG. 6 is a view seen from upper hand of FIG. 5.
Figure 7:
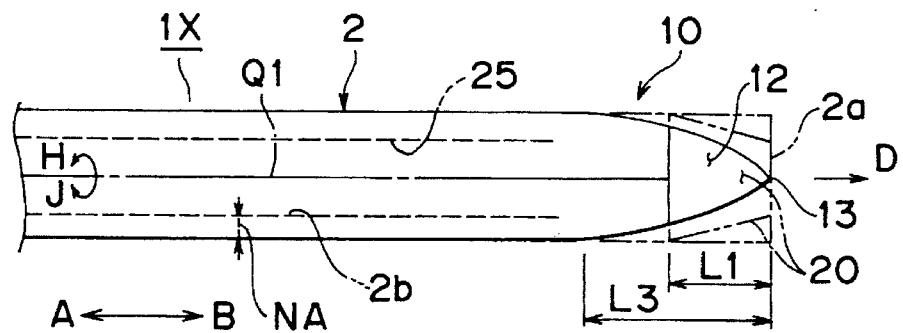
FIG. 7 is a view seen from lower hand of FIG. 5.

For instance, as shown in FIG. 5 through FIG. 7, a medical needle 1X has the cylindrical member 2 inside which the medical liquid flow hole 25 is formed in the direction of axis center Q1, basically similar to the medical needle 1 above-mentioned. At the top edge portion 10 of the cylindrical member 2, the first bevel face 3, where the medical liquid flow hole 25 is open in an oblique direction, formed having the first inclined angle K1 with respect to the axis center Q1, is provided on the center position CS. Besides, at the top edge portion 10 of the cylindrical member 2, the right bevel face 6, formed by being rotated at the first rotational angle M1 in the positive direction with respect to the first bevel face 3 with the axis center Q1 as its center, and formed having the second inclined angle K2 with respect to the axis center Q1 is provided, and the left bevel face 7, formed by being rotated at the second rotational angle M2 in the opposite direction to the first bevel face 3 with the axis center Q1 as its center, and formed having the third inclined angle K3 with respect to the axis center Q1, is provided. At the position opposed to the first bevel face 3 of the top edge portion 10, the sub-bevel face 12 grinded and formed in the oblique direction with respect to the axis center Q1 of the cylindrical member 2, thinning the wall thickness NA of the cylindrical member 2, is provided. The sharp edge portion 13 is comprised of the three grinding faces, or the right bevel face 6, the left bevel face 7 and the sub-bevel face 12. Similar to the medical needle 1 above-mentioned, the sub-bevel face 12 is a part of the tapered first grinding face 20 with the axis center Q1 as its center.

However, since in the medical needle 1X, as shown in FIGS. 5, 6, the sharp edge portion 13 is formed positioning on an inner wall 2b forming the medical liquid flow hole 25 of the cylindrical member 2, a ridgeline portion 16 (as shown in FIGS. 1 and 2) which would be produced by crossing the right bevel face 6 and the left bevel face 7 is not formed near the sharp edge portion 13, then the sharp edge portion 13 is extremely sharply formed.

Since the sub-bevel face 12 in the medical needles 1 and 1X is a part of the tapered first grinding face 20 with the axis center Q1 as its center, in the portion formed the sub-bevel face 12, or the portion near the sharp edge portion 13, especially in the peripheral direction of the cylindrical member 2, as shown in FIG. 7 (there is no figure concerning the medical needle 1, but the medical needle 1 is similar to the medical needle 1X.), a non-grinding face (such as the outer peripheral face of the cylindrical member 2 except the first bevel face 3, the right bevel face 6, the left bevel face 7 and the sub-bevel face 12) being adjacent to the sub-bevel face 12, is not left. Therefore, a stepped portion or the like where the sub-bevel face 12 and the non-grinding face would adjoin, is not formed, then the pain at the time of injection can be further prevented conveniently.

Besides, the medical hollow needle according to the present invention may have an another form except the medical needles 1, 1P and 1X as shown in the respective embodiment mentioned before.

Figure 8:
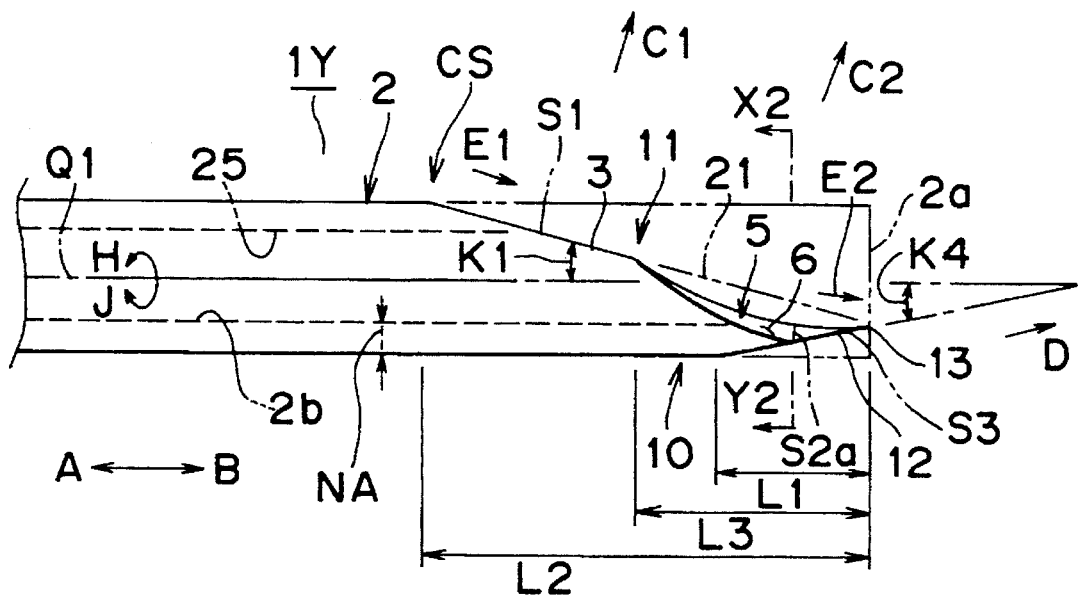
FIG. 8 is a side view showing an another example of the medical hollow needle according to the present invention.
Figure 9:
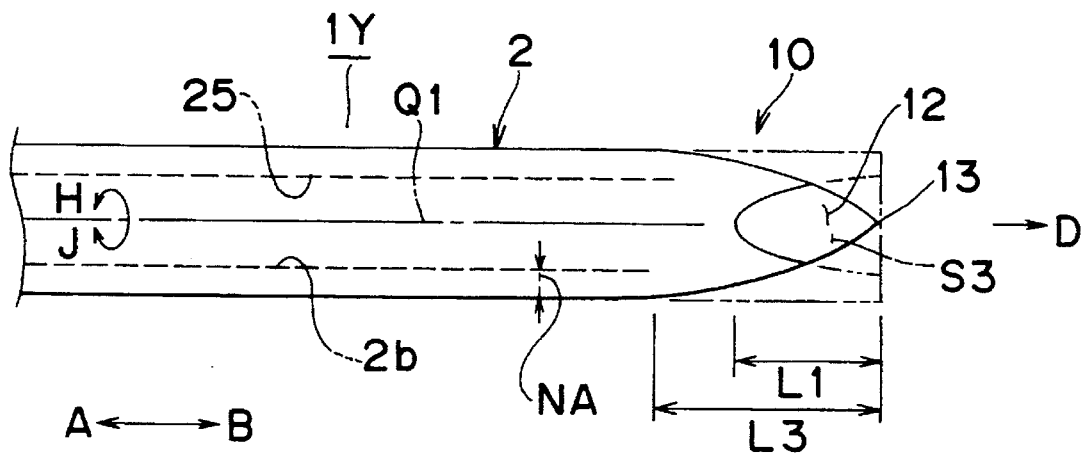
FIG. 9 is a view seen from lower hand of FIG. 8.
Figure 10:
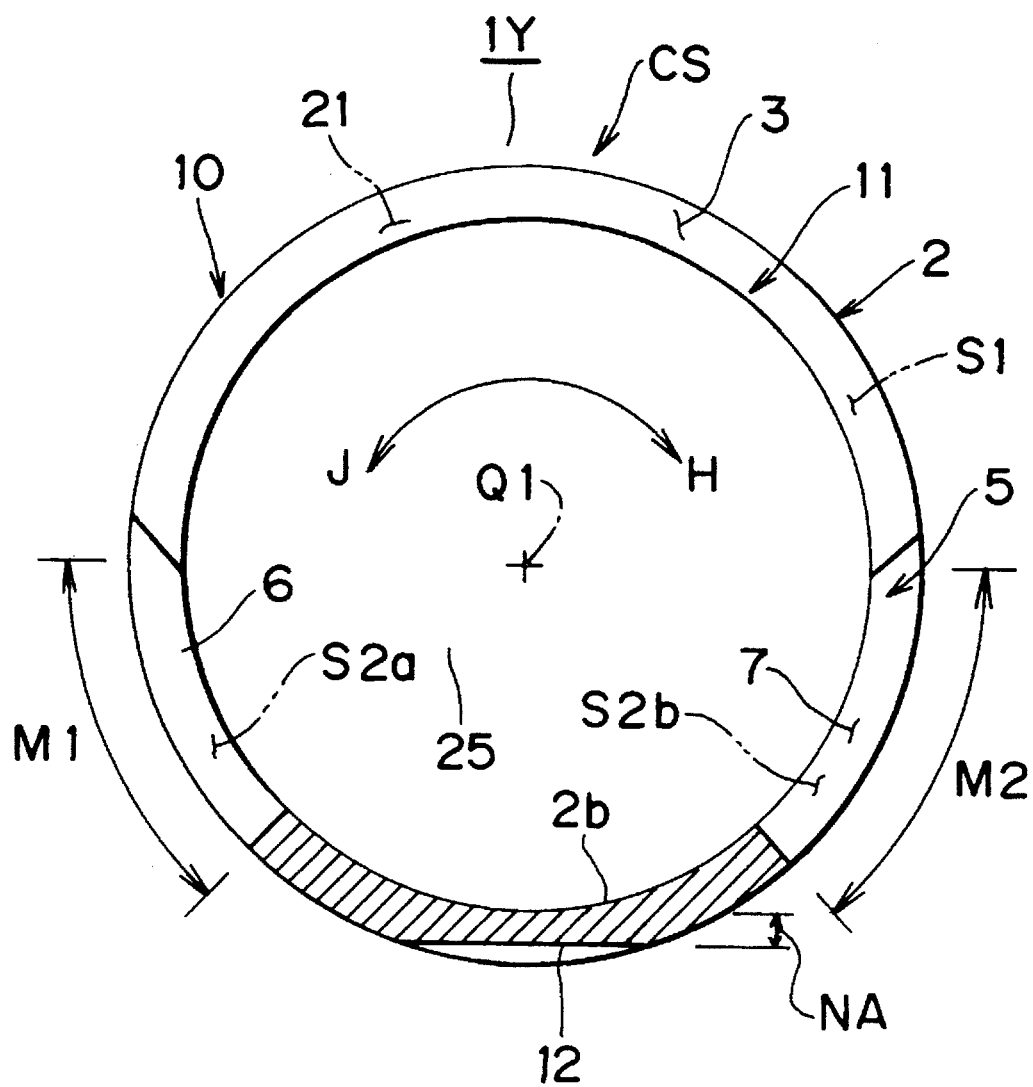
FIG. 10 is a sectional view of line X2—Y2 of FIG. 8.

For instance, as shown in FIG. 8 through FIG. 10, a medical needle 1Y has the cylindrical member 2 inside which the medical liquid flow hole 25 is formed in the direction of the axis center Q1, basically similar to the medical needle 1P before-mentioned. At the top edge portion 10 of the cylindrical member 2, the first bevel face 3, where the medical liquid flow hole 25 is open in an oblique direction, formed having the first inclined angle K1 with respect to the axis center Q1, is provided. Besides, at the top edge portion 10 of the cylindrical member 2, the right bevel face 6, formed by rotating the first rotational angle M1 in the positive direction with respect to the first bevel face 3 with the axis center Q1 as its center, and formed having the second inclined angle K2 with respect to the axis center Q1 is provided, and the left bevel face 7, formed by rotating the second rotational angle M2 in the opposite direction to the first bevel face 3 with the axis center Q1 as its center, and formed having the third inclined angle K3 with respect to the axis center Q1, is provided. At the position opposed to the first bevel face 3 of the top edge portion 10, the sub-bevel face 12 grinded and formed in the oblique direction to the axis center Q1 direction of the cylindrical member 2, thinning the wall thickness NA of the cylindrical member 2, is provided. The sharp edge portion 13 is comprised of the three grinding faces, or the right bevel face 6, the left bevel face 7 and the sub-bevel face 12. The sub-bevel face 12 is in the shape of a plane, similar to the medical needle 1P before-mentioned.

However, since in the medical needle 1Y, as shown in FIG. 8, the sharp edge portion 13 is formed positioning on a inner wall 2b forming the medical liquid flow hole 25 of the cylindrical member 2, a ridgeline portion 16 (as shown in FIG. 3) which would be produced by crossing the right bevel face 6 and the left bevel face 7 is not formed near the sharp edge portion 13, then the sharp edge portion 13 is extremely sharply formed.

Since the sub-bevel face 12 in the medical needles 1P and 1Y is in the shape of a plane, in the portion formed the sub-bevel face 12, or the portion near the sharp edge portion 13, especially in the peripheral direction of the cylindrical member 2, as shown in FIGS. 9 and 10 (there is no figure concerning the medical needle 1P, but the medical needle 1P is similar to the medical needle 1Y.), a non-grinding face (such as the outer peripheral face of the cylindrical member 2 except the first bevel face 3, the right bevel face 6, the left bevel face 7 and the sub-bevel face 12) being adjacent to the sub-bevel face 12, is left. That is, the non-grinding face is left near the sharp edge portion 13, thereby the strength of the medical needles 1P and 1Y in the portion near the sharp edge portion 13 is extremely increased. Besides, since the non-grinding face is left near the sharp edge portion 13 and the strength near the sharp edge portion 13 is not decreased, a sub-bevel inclined angle K4 with respect to the axis center Q1 of the sub-bevel face 12 can be extremely made small (therefore, the area forming the sub-bevel face 12 in the directions as shown by the arrows A and B can be made wider) so as to further make the sharp edge portion 13 thin.

There are results of insertion resistance measuring experiment when a concrete example of the medical needle 1Y before-mentioned is used. That is, insertion resistance measuring experiment has been executed with the needle in which the fourth bevel grinding fade, such as the sub-bevel face 12 is formed (that is, the medical needle 1Y) and the needle in which the fourth bevel grinding face, such as the sub-bevel face 12, is not formed (that is, the conventional medical hollow needle) of the medical hollow needles (the ratio of silicone to flon is 6 percent) in which the length of face of a cutting edge (that is, the second length L2) is 5.5 mm, the second bevel angle (that is, the second and the third inclined angles K2, K3) is 25.5–26 degrees, the length of lancet (that is, the ratio of the third length L3 to the second length L2) is 40–43 percent, the rotation angle (that is, the first and the second rotational angles M1, M2) is 27.5 degrees, under the condition of room temperature of 25 degrees.

As the results of the experiment, the values of insertion resistance in the needle in which the fourth bevel grinding face is formed, are 150.5 g, 156.8 g, 136.2 g, 149.0 g, 137.3 g, 151.0 g, 137.8 g (the average insertion resistance value is 145.5 g), and the values of insertion resistance in the needle in which the fourth bevel grinding face is not formed, are 261.2 g, 235.6 g, 201.3 g, 200.7 g and 217.1 g (the average insertion resistance value is 223.18 g). From the results, it is found that the insertion resistance in the medical hollow needle in which the fourth bevel grinding face is formed is smaller than one in the conventional medical hollow needle in which the fourth bevel grinding face is not formed. In the later experimens, it was found that the insertion resistance value is decreased about 40 percent. Therefore, the insertion resistance in the medical hollow needle according to the present invention is small, thereby at the execution of injection or the like, a patient or the like gets less hurt in blood vessels and the like at the injection part and feels less pain in the injection part.

In the embodiment before-mentioned, the medical needle of so-called lancet type is shown as the concrete example of the medical hollow needle according to the present invention, but the medical hollow needle according to the present invention may be one except the lancet type. For instance, the medical hollow needle according to the present invention may be the medical needle of so-called K3 type, K3' type, a needle having a lateral hole, and a back-cut type.

A medical needle 1Z of the back-cut type of the medical hollow needles according to the present invention is now explained hereinafter.

Figure 11:
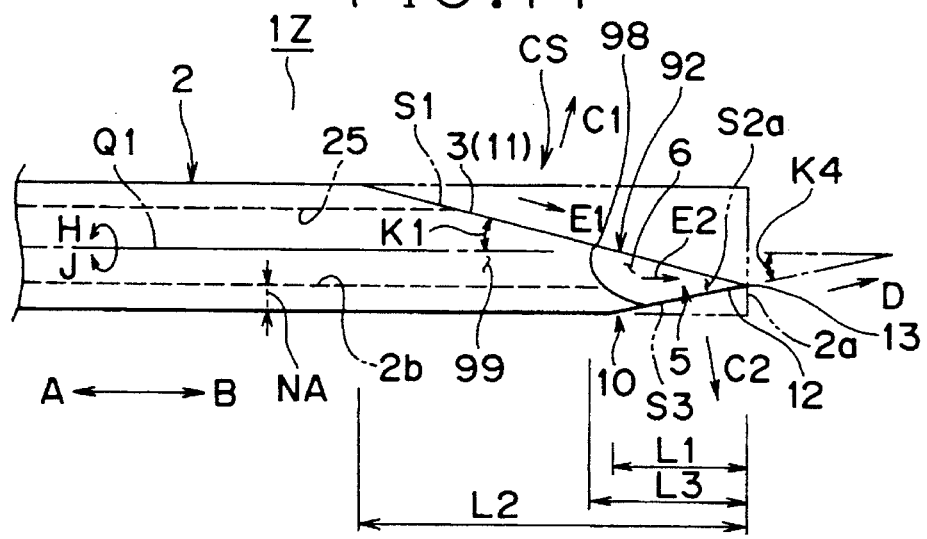
FIG. 11 is a side view showing an another example of the medical hollow needle according to the present invention.
Figure 12:
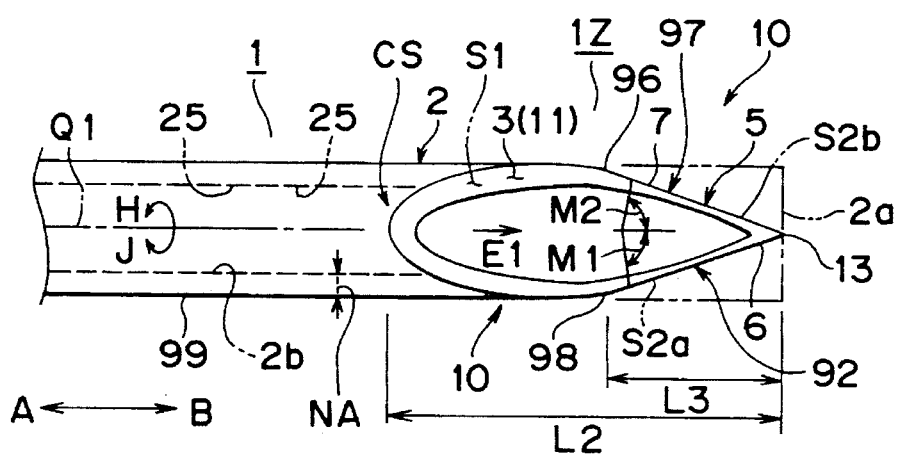
FIG. 12 is a view seen from upper hand of FIG. 11.
Figure 13:
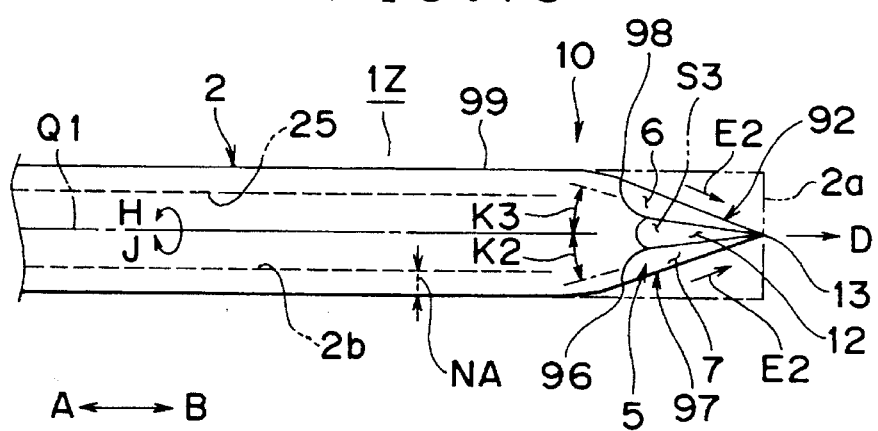
FIG. 13 is a view seen from lower hand of FIG. 11.

As shown in FIGS. 11 through 13, the medical needle 1Z has the cylindrical member 2 inside which the medical liquid flow hole 25 is formed in the direction of axis center Q1. At the top edge portion 10 of the cylindrical member 2, the first bevel face 3, where the medical liquid flow hole 25 is open in an oblique direction, formed having the first inclined angle K1 with respect to the axis center Q1, is provided on the center position CS. Besides, at the top edge portion 10 of the cylindrical member 2, the right bevel face 6, formed by rotating the first rotational angle M1 (90 degrees or more than 90 degrees) in the positive direction with respect to the first bevel face 3 with the axis center Q1 as its center (then, to the center position CS), and formed having the second inclined angle K2 with respect to the axis center Q1 is provided, and the left bevel face 7, formed by rotating the second rotational angle M2 (90 degrees or more than 90 degrees, In the present embodiment, it is shown that the first rotational angle M1 and the second rotational angle M2 are equal with each other, but the first rotational angle M1 and the second rotational angle M2 may be different from each other) in the opposite direction to the first bevel face 3 (then, to the center position CS) with the axis center Q1 as its center, and formed having the third inclined angle K3 with respect to the axis center Q1, is provided (In the present embodiment, the second inclined angle K2 and the third inclined angle K3 are equal to each other, but both angles K2 and K3 may be different from each other). Then, the second bevel face 5 comprised of the right bevel face 6 and the left bevel face 7 is located at the position opposed to the first bevel face 3, and therefore, the open bevel end face 11 by only the first bevel face 3 is formed. At the position opposed to the first bevel face 3 of the top edge .portion 10, the sub-bevel face 12 in the shape of a plane, grinded and formed in the oblique direction with respect to the axis center Q1 of the cylindrical member 2, thinning the wall thickness NA of the cylindrical member 2, is provided respectively adjoining to the right bevel face 6 and the left bevel face on both sides, as shown in FIG. 13. The sharp edge portion 13 is comprised of the four grinding faces, or the first bevel face 3, the right bevel face 6, the left bevel face 7 and the sub-bevel face 12.

Figure 14:
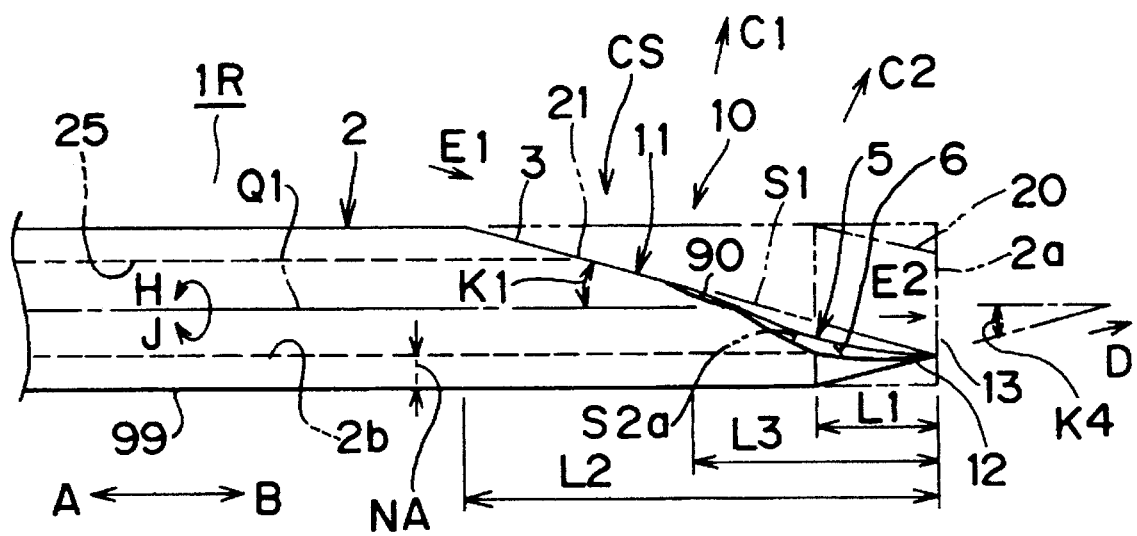
FIG. 14 is a side view showing an another example of the medical hollow needle according to the present invention.
Figure 15:
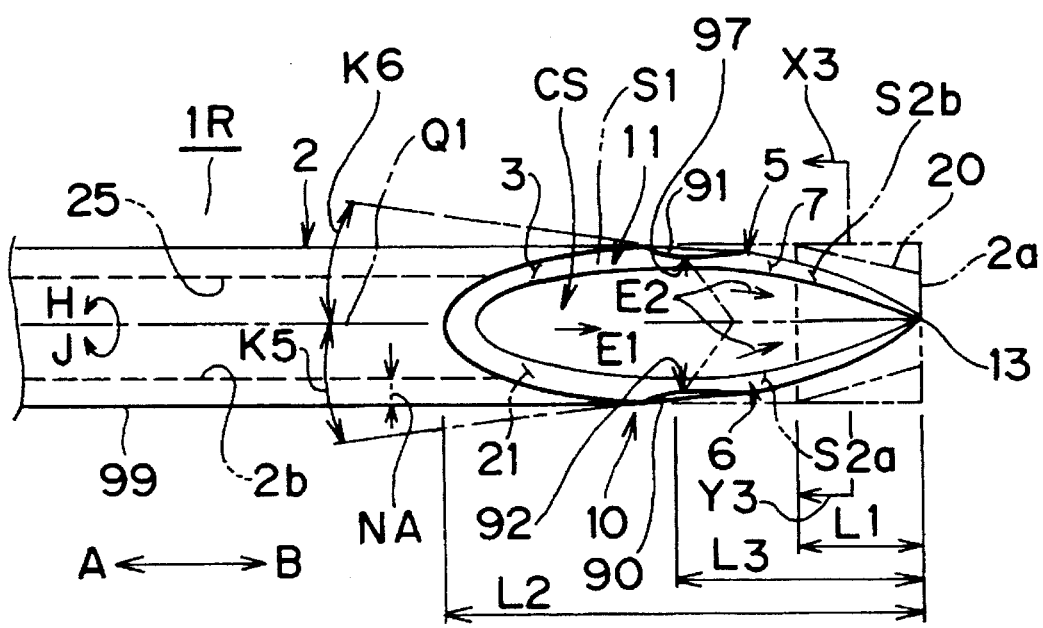
FIG. 15 is a view seen from upper portion of FIG. 14.

In case where the medical hollow needle according to the present invention is the medical needle of so-called lancet type, such as the medical needles 1, 1P, 1X and 1Y shown in the before-mentioned embodiments, the medical needle can be comprised of a medical needle 1R, for instance, as shown in FIGS. 14 and 15 except the medical needles 1, 1P, 1X and 1Y.

Figure 16:
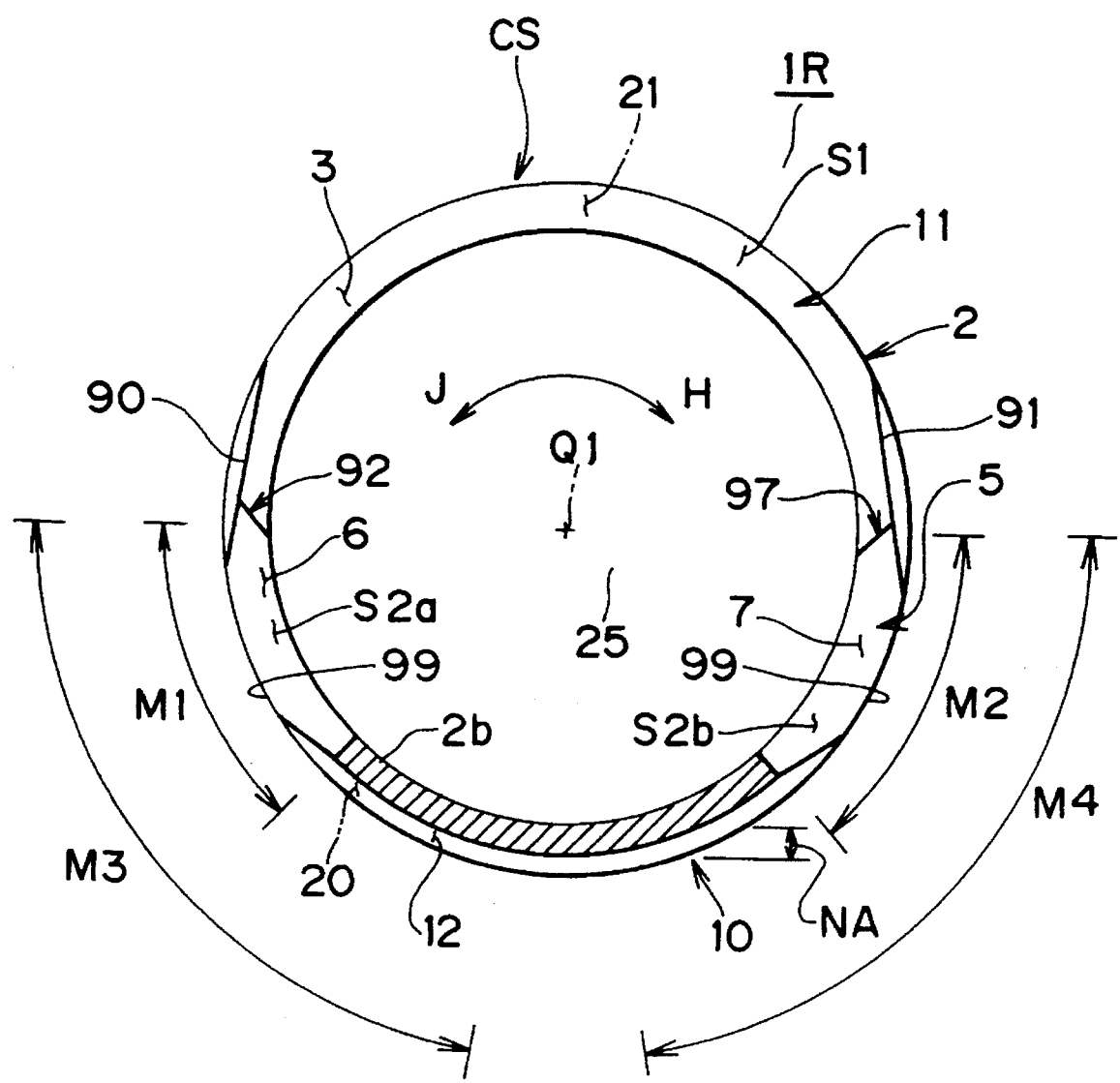
FIG. 16 is a sectional view of line X3—Y3 of FIG. 15.

That is, the medical needle 1R of the lancet type has the cylindrical member 2 inside which the medical liquid flow hole 25 is formed in the direction of the axis center Q1, basically similar to the medical needle 1X before-mentioned, as shown in FIG. 14 through FIG. 16. At the top edge portion 10 of the cylindrical member 2, the first bevel face 3, where the medical liquid flow hole 25 is open in an oblique direction, formed having the first inclined angle K1 with respect to the axis center Q1, is provided on the center position CS. Besides, at the top edge portion 10 of the cylindrical member 2, the right bevel face 6, formed by rotating the first rotational angle M1 in the positive direction with respect to the first bevel face 3 with the axis center Q1 as its center, and formed having the second inclined angle K2 with respect to the axis center Q1 is provided, and the left bevel face 7, formed by rotating the second rotational angle M2 in the opposite direction to the first bevel face 3 with the axis center Q1 as its center, and formed having the third inclined angle K3 with respect to the axis center Q1, is provided. At the position opposed to the first bevel face 3 of the top edge portion 10, the sub-bevel face 12 grinded and formed in the oblique direction with respect to the axis center Q1 of the cylindrical member 2, thinning the wall thickness NA of the cylindrical member 2, is provided. The sharp edge portion 13 is comprised of the three grinding faces, or the right bevel face 6, the left bevel face 7 and the sub-bevel face 12. The sub-bevel face 12 is a part of the tapered first grinding face 20 with the axis center Q1 as its center, similar to the medical needle 1X before-mentioned, the sharp edge portion 13 is formed positioning on the inner wall 2b forming the medical liquid flow hole 25 of the cylindrical member 2.

The medical needle 1R has the following structure in addition to the structure before-mentioned. That is, at the top edge portion 10 of the cylindrical member 2, a right auxiliary grinding face 90 and a left auxiliary grinding face 91 are provided. The right auxiliary grinding face 90 and the left auxiliary grinding face 91 are grinded and formed after the first bevel face 3, the right bevel face 6, the left bevel face 7 and the sub-bevel face 12 are grinded and formed (therefore, after the needle becomes to be similar condition to the medical needle 1X before-mentioned) (This grinding order is not important in the present invention. Any order is applicable.). That is, the right auxiliary grinding face 90 is provided by removing a right apical portion 98 (shown in FIG. 5 or FIG. 6) of an outer peripheral face 99 side of the cylindrical member 2 of a right intersectional portion 92 formed by crossing the first bevel face 3 and the right bevel face 6, and the left auxiliary grinding face 91 is provided by removing a left apical portion 96 (shown in FIG. 6) of the outer peripheral face 99 side of the cylindrical member 2 of a left intersectional portion 97 formed by crossing the first bevel face 3 and the left bevel face 7. Besides, the right auxiliary grinding face 90 is formed by rotating the third rotational angle M3 in the positive direction with respect to the first bevel face 3 with the axis center Q1 as its center, having a fifth inclined angle K5, which is almost intermediate angle between the first inclined angle K1 and the second inclined angle K2, with respect to the axis center Q1. The left auxiliary grinding face 91 is formed by rotating a fourth rotational angle M4 in the opposite direction to the first bevel face 3 with the axis center Q1 as its center, having a sixth inclined angle K6 which is almost intermediate angle between the first inclined angle K1 and the third inclined angle K3, with respect to the axis center Q1.

Since the right auxiliary grinding face 90 and the left auxiliary grinding face 91 are formed in the medical needle 1R by respectively removing the right apical portion 98 and the left apical portion 96 as described hereinbefore, insertion resistance with the medical needle 1R is lower than the needle, such as the medical needle 1X having the right apical portion 98 and the left apical portion 96. That is, when the medical needle 1R is stuck into a human body or the like at the time of execution of injection or the like, the resistance to a skin or blood tissu is made low by not providing the right apical portion 98 and the left apical portion 96, thereby a patient gets litte hurt at the skin and the blood tissu, then little pain is felt at the injection part.

Furthermore, the medical hollow needle having the fifth bevel grinding face, such as the right auxiliary grinding face 90, and the sixth bevel grinding face, such as the left auxiliary grinding face 91, can be applied to any form of a needle having the apical portions 96 and 98 of the outer peripheral side of the intersectional portions 92, 97 formed by the first bevel face and the second-bevel face (that is, the right bevel face 6 and the left bevel face 7), such as the back-cut type in addition to the lancet type before-mentioned.

For instance, in the medical needle 1Z of the back-cut type as shown in FIG. 11 through FIG. 13, the right apical portion 98 of the outer peripheral face 99 side of the cylindrical member 2 of the right intersectional portion 92 formed by crossing the first bevel face 3 and the right bevel face 6 is grinded and removed so as to provide the fifth bevel grinding face, and the left apical portion 96 of the outer peripheral face 99 side of the cylindrical member 2 of the left intersectional portion 97 formed by crossing the first bevel face 3 and the left bevel face 7 is grinded and removed so as to provide the sixth bevel grinding face. The medical hollow needle of the back-cut type is provided with the fifth and the sixth bevel grinding faces, thereby the effects similar to ones of the medical needle 1R before-mentioned are exercised.

The medical hollow needle according to the present invention can be applied to various needles, such as a needle for blood-collecting, a dental needle, and a metallic needle of a remaining needle used for blood transfusion or dialysis in addition to the needle for hypodermic injection.

In the medical needles 1, 1P, 1X, 1Y, 1Z and 1R as shown in the respective embodiments before-mentioned, the sub-bevel inclined angle K4 of the sub-bevel face 12 to the direction of the axis center Q1 of the cylindrical member 2 is set 2–15 degrees, thereby the sharp edge portion 13 can be formed having a proper state in sharpness and strength.

The present invention has been explained on the basis of the embodiments presented herein. However, the embodiments which are described in the present specification are illustrative and not limiting. The scope of the invention is designated by the accompanying claims and is not restricted by the descriptions of the specific embodiments. Accordingly, all the transformations and changes belonging to the claims are included in the scope of the present invention.

I claim:

1. A medical hollow needle comprising:

a cylindrical member having a flow path capable of passing a fluid therein along a axis center direction;

a first bevel grinding face formed at a top end portion of said cylindrical member, such that said flow path is open in an oblique direction, having a first inclined angle with respect to said center axis;

a second bevel grinding face formed by rotating a first rotational angle in a positive direction with respect to said first bevel grinding face with said center axis as its center, having a second inclined angle with respect to said center axis, and a third bevel grinding face formed by rotating a second rotational angle in an opposite direction with respect to said first bevel grinding face with said axis center as its center, having a third inclined angle with respect to said center axis, both formed at said top edge portion of said cylindrical member;

a fourth bevel grinding face in a shape of a plane, grinded and formed at a position opposed to said first bevel grinding face of said top edge portion of said cylindrical member in an oblique direction with respect to said center axis direction of said cylindrical member, thereby thinning a thickness of said cylindrical member; and a sharp edge portion comprised of at least three grinding faces, that is, said second, said third and said fourth bevel grinding faces.

2. The medical hollow needle as set forth in claim 1, wherein said fourth bevel grinding face is formed at an inclined angle 2–15 degrees with respect to said center axis direction of said cylindrical member.

3. The medical hollow needle as set forth in claim 1, wherein said second and said third inclined angles are equal to each other.

4. The medical hollow needle as set forth in claim 1, wherein said first and said second rotational angles are equal to each other.

5. A method of producing a medical hollow needle, said method comprising:

grinding a top edge portion of a cylindrical member defining a flow path capable of passing a fluid therein along a center axis direction, in an oblique direction with respect to said center axis direction of said cylindrical member, thinning wall thickness of said cylindrical member, so as to form a fourth bevel grinding face in the shape of a plane;

performing a grinding machining on a portion opposed to said fourth bevel grinding face of said top edge portion of said cylindrical member formed said fourth bevel grinding face, in an oblique direction, having a first inclined angle with respect to said center axis so as to form a first bevel grinding face in which said flow path is open in an oblique direction;

performing a grinding machining on said top edge portion of said cylindrical member by rotating a first rotational angle in a positive direction with respect to said first bevel grinding face with said axis center as its center, having a second inclined angle with respect to said center axis so as to form a second bevel grinding face, and by rotating a second rotational angle in an opposite direction with respect to said first bevel grinding face with said axis center as its center, having a third inclined angle with respect to said center axis so as to form a third bevel grinding face, respectively; and forming a sharp edge portion comprised of at least said second, said third and said fourth bevel grinding faces.

6. A method of producing a medical hollow needle, said method comprising:

performing a grinding machining on a top edge portion of a cylindrical member formed a flow path capable of passing a fluid therein in its center axis direction, in an oblique direction having a first inclined angle with respect to said center axis so as to form a first bevel grinding face in which said flow path is open in an oblique direction;

performing a grinding machining on said top edge portion of said cylindrical member by rotating a first rotational angle in a positive direction with respect to said first bevel grinding face with said axis center as its center, having a second inclined angle with respect to said center axis so as to form a second bevel grinding face, and by rotating a second rotational angle in an opposite direction with respect to said first bevel grinding face with said axis center as its center, having a third inclined angle with respect to said center axis so as to form a third bevel grinding face, respectively;

grinding a position opposed to said first bevel grinding face of said top edge portion of said cylindrical member in an oblique direction with respect to said center axis, thinning a wall thickness of said cylindrical member so as to form a fourth bevel grinding face in the shape of a plane; and forming a sharp edge portion comprised of at least said second, said third and said fourth bevel grinding faces.

7. A method of producing a medical hollow needle, said method comprising:

performing a grinding machining on a top edge portion of a cylindrical member forming a flow path capable of passing a fluid therein in its center axis direction, in an oblique direction having a first inclined angle with respect to said center axis so as to form a first bevel grinding face in which said flow path is open in an oblique direction;

grinding a position opposed to said first bevel grinding face of said top edge portion of said cylindrical member in an oblique direction with respect to said center axis, thinning wall thickness of said cylindrical member so as to form a fourth bevel grinding face in the shape of a plane;

performing a grinding machining on said top edge portion of said cylindrical member by rotating a first rotational angle in a positive direction with respect to said first bevel grinding face with said axis center as its center, having a second inclined angle with respect to said center axis so as to form a second bevel grinding face, and by rotating a second rotational angle in an opposite direction with respect to said first bevel grinding face with said axis center as its center, having a third inclined angle with respect to said center axis so as to form a third bevel grinding face, respectively; and forming a sharp edge portion comprised of at least said second, said third and said fourth bevel grinding faces.

8. A method of producing a medical hollow needle, said method comprising:

performing a grinding machining on a top edge portion of a cylindrical member forming a flow path capable of passing a fluid therein in its center axis direction by rotating a first rotational angle in a positive direction with respect to a predetermined standard position with said axis center as its center, having a second inclined angle with respect to said center axis so as to form a second bevel grinding face, and by rotating a second rotational angle in an opposite direction with respect to said standard position with said axis center as its center, having a third inclined angle with respect to said center axis so as to form a third bevel grinding face, respectively;

grinding a position opposed to said standard position of said top edge portion of said cylindrical member in an oblique direction with respect to said center axis direction, thinning wall thickness of said cylindrical member so as to form a fourth bevel grinding face in the shape of a plane;

performing a grinding machining on said top edge portion of said cylindrical member at said standard position in an oblique direction, having a first inclined angle with respect to said center axis so as to form a first bevel grinding face in which said flow path is open in an oblique direction; and forming a sharp edge portion comprised of at least said second, said third, and said fourth bevel grinding faces.

9. A method of producing a medical hollow needle, said method comprising:

performing a grinding machining on a top edge portion of a cylindrical member formed a flow path capable of passing a fluid therein in its center axis direction by rotating a first rotational angle in a positive direction with respect to a predetermined standard position with said axis center as its center, having a second inclined angle with respect to said center axis so as to form a second bevel grinding face, and by rotating a second rotational angle in an opposite direction with respect to said standard position with said axis center as its center, having a third inclined angle with respect to said center axis so as to form a third bevel grinding face, respectively;

performing a grinding machining on said top edge portion of said cylindrical member at said standard position in an oblique direction, having a first inclined angle with respect to said center axis so as to form a first bevel grinding face in which said flow path is open in an oblique direction;

grinding a position opposed to said first bevel grinding face of said top edge portion of said cylindrical member in an oblique direction with respect to said center axis direction, thinning wall thickness of said cylindrical member so as to form a fourth bevel grinding face in the shape of a plane; and forming a sharp edge portion comprised of at least said second, said third, and said fourth bevel grinding faces.

10. The method of producing the medical hollow needle as set forth in one of claim 5, 6, 7, 8, or 9 wherein said fourth bevel grinding face is grinded with an inclined angle of 2–15 degrees with respect to said center axis direction of said cylindrical member.

11. The method of producing the medical hollow needle as set forth in one of claim 5, 6, 7, 8, or 9 wherein said second and third inclined angles are equal to each other.

12. The method of producing the medical hollow needle as set forth in claim 5, 6, 7, 8, or 9 wherein said first and said second rotational angles are equal to each other.

* * * * *